United States Patent
Aguilar et al.

(10) Patent No.: US 9,861,274 B2
(45) Date of Patent: Jan. 9, 2018

(54) METHOD FOR ASSISTING VISUAL EXPLORATION FOR AN INDIVIDUAL SUFFERING FROM A RETINAL CONDITION RESULTING IN A SCOTOMA

(71) Applicants: ESSILOR INTERNATIONAL (COMPAGNIE GENERALE D'OPTIQUE), Charenton le Pont (FR); CENTRE NATIONAL DE LA RECHERCHE SCIENTIFIQUE—CNRS, Paris (FR); UNIVERSITE D'AIX-MARSEILLE, Marseilles (FR)

(72) Inventors: Carlos Aguilar, Marseilles (FR); Eric Castet, Marseilles (FR)

(73) Assignees: ESSILOR INTERNATIONAL (COMPAGNIE GENERALE D'OPTIQUE), Charenton-le-Pont (FR); CENTRE NATIONAL DE LA RECHERCHE SCIENTIFIQUE—CNRS, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 0 days.

(21) Appl. No.: 14/912,452

(22) PCT Filed: Aug. 7, 2014

(86) PCT No.: PCT/EP2014/067017
§ 371 (c)(1),
(2) Date: Feb. 17, 2016

(87) PCT Pub. No.: WO2015/024790
PCT Pub. Date: Feb. 26, 2015

(65) Prior Publication Data
US 2016/0198941 A1    Jul. 14, 2016

(30) Foreign Application Priority Data

Aug. 21, 2013    (EP) .................................... 13306159

(51) Int. Cl.
*A61B 3/00*    (2006.01)
*A61B 3/10*    (2006.01)
(Continued)

(52) U.S. Cl.
CPC .......... *A61B 3/0025* (2013.01); *A61B 3/0041* (2013.01); *A61B 3/0091* (2013.01);
(Continued)

(58) Field of Classification Search
CPC ....... A61B 3/0025; A61B 3/10; A61B 3/0091; A61B 3/0041; G06T 7/0051;
(Continued)

(56) References Cited

U.S. PATENT DOCUMENTS

2012/0200595 A1    8/2012  Lewis et al.

FOREIGN PATENT DOCUMENTS

| FR | 2 846 120 A1 | 4/2004 |
| WO | 96/34555 A1 | 11/1996 |
| WO | 2008/119187 A1 | 10/2008 |

OTHER PUBLICATIONS

International Search Report, dated Oct. 22, 2014, from corresponding PCT Application.

*Primary Examiner* — Jack Dinh
(74) *Attorney, Agent, or Firm* — Young & Thompson (57) ABSTRACT

A method of assisting visual exploration for individuals suffering from a retinal condition resulting in a scotoma and, more particularly, a method S for assisting visual exploration by such an individual of a digital image on a display device, the method including: —recognizing, using shape recognition software, at least one object contained in an object area (Continued)

of the digital image, —determining a blind area in the image, corresponding to a position of the scotoma in the field of vision of the user looking at the image, —if the blind area and the object area are detected to be in close proximity to each other, applying image processing to the image consisting in highlighting the object area for the user.

22 Claims, 7 Drawing Sheets

(51) Int. Cl.
      *G06T 3/40*       (2006.01)
      *G06T 7/00*       (2017.01)
      *G09B 21/00*       (2006.01)

(52) U.S. Cl.
      CPC .................. *A61B 3/10* (2013.01); *G06T 3/40* (2013.01); *G06T 7/0051* (2013.01); *G06T 7/0081* (2013.01); *G09B 21/008* (2013.01); *G06T 2207/20144* (2013.01); *G06T 2207/30201* (2013.01)

(58) Field of Classification Search
      CPC ..................... G06T 7/0081; G06T 3/40; G06T 2207/30201; G06T 2207/20144
      USPC .................................................. 351/205, 246
      See application file for complete search history.

FIG. 1

FIG. 2 r     +     +are

FIG. 3a

+            + simple    simple

METHOD FOR ASSISTING VISUAL EXPLORATION FOR AN INDIVIDUAL SUFFERING FROM A RETINAL CONDITION RESULTING IN A SCOTOMA

BACKGROUND OF THE INVENTION

Field of the Invention

The invention relates to the field of methods for assisting visual exploration for individuals afflicted with a retinal pathology manifested by a scotoma, such as age related macular degeneration (ARMD), Stargardt's disease or maculopathies.

The invention relates more particularly to a method for assisting visual exploration of a digital image on a display device by an individual afflicted with a retinal pathology manifested by a scotoma.

ARMD, Stargardt's disease or maculopathies can give rise to visual deficiencies manifested by the progressive destruction of the central vision and by the development of a blind spot called a "scotoma" which deletes the information which arrives at the foveal region. This information is essential for carrying out certain daily tasks such as reading or more generally recognition of objects in an image. The absence of therapies capable of definitively eliminating this affliction compels the individual to opt for methods of assistance, often of an optical nature.

A need therefore exists to provide a method which facilitates visual exploration of an image, such as for example navigation within a text, which is able to adapt to the pathology of the individual and which uses visual neuroscience principles to best assist the individual, or indeed to increase their reading performance.

Description of the Related Art

A known solution is described in document US 2012/0200595. The system consists of smart spectacles fitted with an oculometer. If the user is an individual afflicted with ARMD, the system takes account of the zone of the individual's visual field which is masked by his/her macular scotoma. Firstly, the spectacles capture the image of a scene and project it onto ophthalmic lenses. Thereafter, the oculometer implanted on these spectacles makes it possible to measure the position of the gaze on the projected image. The user can activate the enhancement of the image zone which is masked by his/her scotoma. The enhancement of this image zone can be either the increasing of its size, or the increasing and the shifting of its lines, or a displacement and a deformation of its lines around the scotoma.

According to this system, the position of the gaze and the size of the scotoma are used to define the enhanced information in proximity to the scotoma. It is thus capable of adapting to the characteristics of each individual's scotoma. However, although the image processing proposed by this system takes account of the retinal pathology of the individual, the enhancement performed takes no account of fundamental aspects of reading in the presence of a macular scotoma. Indeed, this system acts only on the pixels of the image zone, to displace the information masked by the scotoma. Consequently, it does not make it possible to optimize the interaction between the position of the gaze, the size of the scotoma and the entities "words" and "letters" of the text. Furthermore, this system does not propose a slaving to the gaze which takes account of oculomotor events in the absence of central vision, yet this is necessary in order to optimize the ocular movements of individuals afflicted with retinal pathology. Therefore, this system risks a lack of effectiveness in terms of comfort and especially in terms of reading performance.

BRIEF SUMMARY OF THE INVENTION

In this context, the present invention is aimed at alleviating one or more of the drawbacks previously mentioned by proposing a method for assisting visual exploration of a digital image on a display device by an individual afflicted with a retinal pathology manifested by a scotoma, the digital image being composed of a matrix of points which is segmentable into zones.

To this end, the method of the invention is essentially such that it comprises the steps consisting in:
  recognizing, with the aid of shape recognition software, at least one object contained in an object zone of the digital image,
  determining a blind zone in the image, corresponding to a position of the scotoma in the field of vision of the user looking at the image,
  in case of detection of a proximity of the blind zone and of the object zone, applying a processing of the image, for highlighting the object zone for the user.

The method thus advantageously makes it possible not only to use the position of the gaze and the size of the scotoma to define the information to be reproduced in an enhanced manner, but also to detect various objects of the image, to specifically identify those that the individual is exploring or wishes to explore visually and to optimize the enhanced display of this object so as to compensate the factors that limit vision thereof.

The words "shapes" and "object" such as used hereinabove are to be considered in a very general sense. One is not dealing with geometric shape alone, but any type of global, local or semi-local extractable visual characteristics of the digital image. The shapes or patterns to be recognized can be of very varied natures. They may consist at one and the same time of objects, faces, word lines, words, letters, etc.

According to a particular feature of the method, it furthermore comprises the steps consisting in:
  determining a zone of interest comprising at least one object zone, according to a criterion of positioning of the blind zone on the digital image, the blind zone being positionable on the display device by slaving to a pointing device,
  displaying on the display device a marking allowing the viewing of the determined zone of interest, and
  the highlighting of the object zone consists in enhancing the determined zone of interest by modifying it and by reproducing it in a vision zone according to at least one predetermined processing.

The method thus advantageously makes it possible to visually inform the individual that he/she can enhance an object recognized by the automatic marking thereof.

According to another particular feature of the method, the criterion, according to which the zone of interest is determined, of positioning of the blind zone on the digital image is chosen from among:
  a criterion of overlap of the zone of interest by the blind zone, and
  a criterion of overlap of the zone of interest by a preferred retinal locus zone determined for each individual, the positioning of this preferred retinal locus zone on the display device relating to the positioning of the blind zone on this same device.

According to the previous particular feature, said criterion of overlap consists in determining:

the positioning of a specific point of the blind zone or of the preferred retinal locus zone on the zone of interest, or a larger area of overlap of the zone of interest by the blind zone or by the preferred retinal locus zone.

According to another particular feature of the method, when the zone of interest is situated in proximity to an edge of the display device so that the vision zone would be only partially reproduced on the display device according to said predetermined processing, the enhancement of the zone of interest furthermore consists in displacing the vision zone in such a way that it is completely reproduced on the display device and exhibits a substantially maximum overlap with the vision zone which would be only partially reproduced on the display device according to said predetermined processing.

According to another particular feature of the method, the highlighting of the object zone is controlled by the individual by actuating, and optionally by keeping actuated, an actuator, and the method furthermore comprises a step of return to the digital image before enhancement, this return being controlled by the individual by actuation, and optionally by release, of the actuator, respectively.

The method according to this particular feature thus advantageously allows the individual to control the duration of the enhancement.

According to another particular feature of the method, at least one zone out of the blind zone and the vision zone comprises a visible marking on the display device.

The method according to this particular feature thus advantageously makes it possible to aid the individual to be aware of the extent of his/her scotoma so as to allow him/her to optimize their ocular movements. Furthermore, in the case where the method is further a method for assisting reading on a display device of a text, the method according to this particular feature furthermore advantageously makes it possible to aid the individual to stabilize vertically on the line that he/she is in the process of reading.

According to a first embodiment of the method, the shape recognition software comprises an algorithm for segmenting objects with respect to the background which is based on the principle of the figure-background segregation employed in automatic image processing.

The method according to this first embodiment is thus advantageously tailored to the local or semi-local recognition of objects, of faces or of geometric shapes.

According to a particular feature of the first embodiment of the method, the predetermined processing of the zone of interest consists of the progressive magnification of its size and optionally its progressive shifting from its initial position in the digital image until it occupies on the display device the vision zone and the method furthermore comprises a step of return to the digital image before enhancement consisting of a progressive decreasing of the size of the enhanced zone of interest and optionally a progressive shifting of its position until its return to its size and its position before enhancement.

The method according to this particular feature of the first embodiment thus advantageously allows the individual to preserve a memory of the initial position of the zone of interest in the digital image, especially so as to facilitate subsequent visual exploration of the remainder of the digital image. The shifting of the position of the enhanced zone of interest furthermore makes it possible to advantageously make the vision zone coincide best with a preferred retinal locus zone determined for each individual.

According to a second embodiment of the method, the method for assisting visual exploration is a method for assisting reading; the digital image comprises a text intended to be read; the shape recognition software comprises character recognition software, making it possible to recognize at least one text part by its segmentation into line zones, and then by the segmentation of each line zone into word zones; the object zone is a word zone; the vision zone is situated at the periphery of the blind zone.

The method according to its second embodiment thus advantageously makes it possible not only to use the position of the gaze and the size of the scotoma to define the information to be reproduced in an enhanced manner in proximity to the scotoma, but also to detect various words of the image, to specifically identify a group of words that the individual wishes to read, to visually inform the individual that he/she can enhance this group of words by the automatic marking of the latter and to optimize the enhanced display of this group of words so as to compensate the factors that limit his/her reading capacity. It should be noted furthermore that segmenting the image into word zones makes it possible to reproduce complete words in the vision zone.

According to a particular feature of its second embodiment, the method furthermore comprises, prior to the determination of the zone of interest, a step consisting in modifying the image of the text by its redimensioning and/or by modification of the line spacing as a function of the size of the characters, of the length and/or of the number of the lines, of the size of the display device and/or of the size of the blind zone.

The method thus advantageously makes it possible to preserve for the display the maximum of global information on the text so that the individual can get his/her bearings easily without being compelled to displace the image permanently.

According to another particular feature of its second embodiment, the recognition of said at least one text part furthermore comprises the segmentation of each word zone into letter zones.

The method according to its second embodiment thus advantageously allows more finely controlled modification and reproduction of the words situated in the zone of interest.

According to another particular feature of the second embodiment of the method, the zone of interest comprises, in addition to said at least one word zone, at least two other word zones belonging to the same line zone, each word zone of the zone of interest being juxtaposed with another word zone of the zone of interest.

The method thus advantageously makes it possible to tailor the assistance afforded the individual to his/her visual span.

According to another particular feature of the second embodiment of the method, said at least one predetermined processing of the zone of interest consists of:

a segmentation of each word zone into character zones, and/or an increasing of the size of the characters as a function of the size of the blind zone, and/or a change of character font, and/or a layout of the words over several lines, and/or a breaking of a word, and/or an increasing of the spacing between the characters, and/or a modification of the contrast, and/or a polarity inversion, and/or a voice synthesis of the words contained in the zone of interest.

The method according to its second embodiment thus advantageously makes it possible to modify each of the words of the zone of interest differently.

According to a variant of the previous particular feature, the size of the characters and/or the spacing between the characters are further increased as the characters are intended to be reproduced on a line of the vision zone further from the blind zone.

The method thus advantageously makes it possible to limit, or indeed to eliminate, the phenomenon of visual crowding.

According to another particular feature of the second embodiment of the method, a previous zone of interest and/or a following zone of interest are furthermore determined, situated respectively on either side of a current zone of interest, at least one of these zones comprising a visible marking on the display device.

The method according to its second embodiment thus advantageously makes it possible to prevent one and the same group of words from being enhanced several times and/or successive zones of interest from exhibiting word zones in common, or makes it possible at least to signal these occurrences to the individual. Furthermore, the method can thus advantageously make it possible to signal to the individual the next group of words to be enhanced.

According to another particular feature of its second embodiment, the method furthermore comprises a step consisting in displaying on the display device a frame on the left of the line zone situated directly below the line zone comprising the zone of interest.

The method according to its second embodiment thus advantageously makes it possible to assist the reader upon passage to the following line, this passage being particularly difficult when reading under eccentric vision.

According to a particular feature of its first and second embodiments, the method comprises, prior to the reproduction in the vision zone of the processed zone of interest or prior to the determination of the zone of interest according to a choice of said positioning criterion, a step consisting in determining the peripheral position of the vision zone with respect to the blind zone as corresponding to the position of a preferred retinal locus zone determined for each individual.

The method thus advantageously makes it possible to optimize, in a manner tailored to each individual, the effectiveness of the slaving to the gaze in the absence of macular vision.

According to the previous particular feature, the determination of the peripheral position of the vision zone with respect to the blind zone comprises the calibration steps consisting in:

displaying on the display device a plurality of targets, for each target, detecting, with an oculometer, the relative position of the scotoma of the individual with respect to the target when the individual fixes on the target, and calibrating the position of the preferred retinal locus zone as being the relative position of the target with respect to the position of the scotoma, and if, the relative position of the scotoma with respect to the position of the target varies as a function of the target, slaving, as a function of the calibration carried out according to the previous detections, the positioning of a shape outline displayed on the display device to the positioning of the scotoma detected by the oculometer, displaying a fixed target symbol on the display device, measuring the shift between the slaved shape outline and the target symbol, when the individual to be positioned the slaved shape outline so as to include therein the target symbol, and correcting, as a function of this measurement, the calibration carried out according to the previous detections.

According to another particular feature of the first and second embodiments of the method, the vision zone is situated in a juxtaposed and centered manner below or above the blind zone.

The method according to its first and second embodiments thus advantageously allows the individual to identify the largest number of visual characteristics, such as letters, in a single fixation and thus to increase his/her visual span. Furthermore, the method according to this other particular feature allows the individual to preserve, even during the display of the vision zone, his/her perceptive span intact.

According to another particular feature of the first and second embodiments of the method, the pointing device slaving the positioning of the blind zone is chosen from among a computer keyboard, a mouse and an oculometer.

The invention relates, according to another aspect, to a computer program comprising instructions for the implementation of the method as claimed in any one of the preceding claims, when this program is executed by a processor.

The advantages afforded by the computer program such as is set forth succinctly hereinabove, are at least identical to those mentioned above in conjunction with the method according to the first aspect of the invention.

BRIEF DESCRIPTION OF THE DRAWINGS

Other characteristics and advantages of the invention will emerge clearly from the description given thereof hereinafter, by way of wholly nonlimiting indication, with reference to the appended drawings, in which.

DETAILED DESCRIPTION OF THE PREFERRED EMBODIMENTS

In its broadest acceptance, the invention relates to a method S for assisting visual exploration of a digital image I on a display device D by an individual afflicted with a retinal pathology manifested by a scotoma. The digital image I is composed of a matrix of points which is segmentable into zones.

The method S comprises the steps consisting in:
- recognizing S10, with the aid of shape recognition software, at least one object contained in an object zone ZO of the digital image,
- determining S30 a blind zone Z1 in the image, corresponding to a position of the scotoma in the field of vision of the user looking at the image,
- in case of detection of a proximity of the blind zone and of the object zone, applying a processing of the image, for highlighting S70, S90 the object zone for the user.

The method S thus allows advantageously not only to use the position of the gaze and the size of the scotoma to define the information to be reproduced in an enhanced manner, but also to detect various objects of the image I, to specifically identify those that the individual is exploring or wishes to explore visually and to optimize the enhanced display of this object so as to compensate the factors that limit vision thereof.

The method S furthermore comprises the steps consisting in:
- determining S50 a zone of interest Z2 comprising at least one object zone ZO, according to a criterion of positioning of the blind zone Z1 on the digital image,
- displaying S60 on the display device a marking MZ2 allowing the viewing of the determined zone of interest Z2.

Furthermore, the highlighting S70, S90 of the object zone consists in enhancing the determined zone of interest Z2 by modifying it S70 and by reproducing it S90 in a vision zone Z3 according to at least one predetermined processing.

In the same manner as the gaze of the individual traverses the digital image I, the blind zone Z1 must be able to be freely positionable by the reader on the display device D and more particularly on the digital image I. This is carried out by slaving the positioning of the blind zone Z1 to a pointing device, such as a computer keyboard, a mouse or preferably an oculometer.

The method thus advantageously makes it possible to visually inform the individual that he/she can enhance an object recognized by the automatic marking thereof. Indeed, the marking MZ2 of the zone of interest Z2 allows the individual to be aware of the recognized object that he/she can enhance.

The marking of a zone whatever it be, and of the zone of interest Z2 in particular, consists in the action of emphasizing the graphical element (or more particularly the text part according to the second embodiment described below) constituting this zone by modifying its visual attributes. By way of examples, the marking can consist of an outline and/or of an overlining of the zone.

According to a particular feature of the method S, the criterion, according to which the zone of interest Z2 is determined, of positioning of the blind zone Z1 on the digital image I is chosen from among:

- a criterion of overlap of the zone of interest Z2 by the blind zone Z1, and
- a criterion of overlap of the zone of interest Z2 by a preferred retinal locus zone PRL determined for each individual, the positioning of this preferred retinal locus zone PRL on the display device D relating to the positioning of the blind zone Z1 on this same device.

According to the previous particular feature, said criterion of overlap consists in determining:
- the positioning of a specific point of the blind zone Z1 or of the preferred retinal locus PRL zone on the zone of interest Z2, said specific point being for example the center or the bottom right corner of the zone considered, or
- a larger area of overlap of the zone of interest Z2 by the blind zone Z1 or by the preferred retinal locus PRL zone.

The criterion of overlap based on determining a larger area of overlap probably requires a few simple geometric calculations, for example based on the coordinates of each recognized object. These calculations are assumed to be within the field of competence of the person skilled in the art.

Figure 9A:
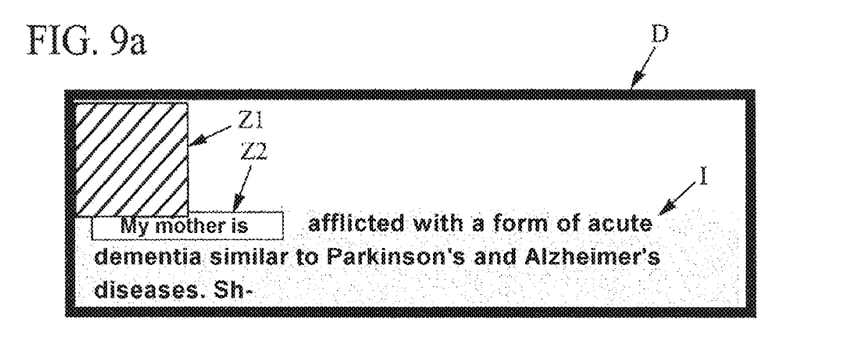
FIGS. 9a and 9b illustrate a particular feature of the method according to the invention in its second embodiment.
Figure 9B:
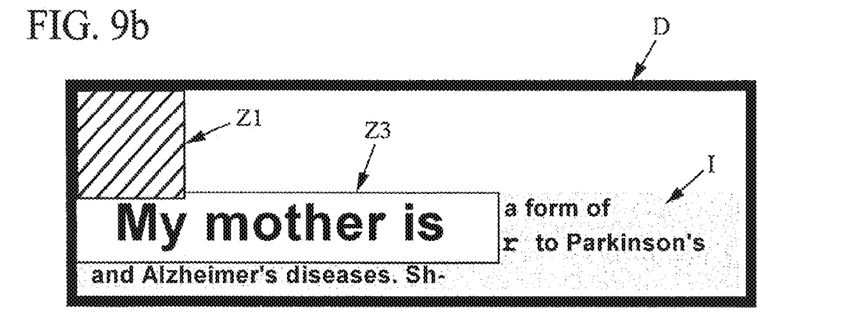

As illustrated in FIGS. 9A and 9B in relation to the second embodiment of the method, but the particular feature illustrated by this figure not being limited to this embodiment, it can provide that the zone of interest Z2 be situated in proximity to an edge of the display device D so that the vision zone Z3 would be only partially reproduced on the display device D according to said predetermined processing. Then, according to a particular feature of the method S, the enhancement of the zone of interest Z2 consists, in addition to the modification S70 and reproduction S90 of the zone of interest Z2, in displacing the vision zone Z3 in such a way that it is completely reproduced on the display device D. This displacement is preferably carried out in such a way that the vision zone Z3 thus displaced exhibits a substantially maximum overlap with the vision zone Z3 which would be only partially reproduced on the display device D according to said predetermined processing. This preference is all the more marked as the position of the vision zone Z3 with respect to the blind zone Z1 is chosen as corresponding to the position of a preferred retinal locus zone determined for each individual for example according to the test described below.

According to another particular feature of the method S, the highlighting of the object zone or the enhancement of the determined zone of interest Z2 is controlled by the individual by actuating an actuator and the method can furthermore comprise a step of return to the digital image I before enhancement, this return being controlled by the individual also by actuation of the actuator. Optionally, the actuation of the actuator can be maintained by the individual, and optionally the step of return to the digital image I before enhancement is controlled by release of the actuator.

The method S according to this particular feature thus advantageously allows the individual to control the triggering and the duration of the enhancement.

According to another particular feature of the method S, in addition to the required marking MZ2 of the zone of interest Z2, at least one zone out of the blind zone Z1 and the vision zone Z3 comprises a visible marking on the display device.

The method thus advantageously makes it possible to aid the individual, not only to stabilize on the recognized object that he/she wishes to enhance, but also to be aware of the extent of his/her scotoma so as to allow him/her to optimize his/her ocular movements.

Figure 10:
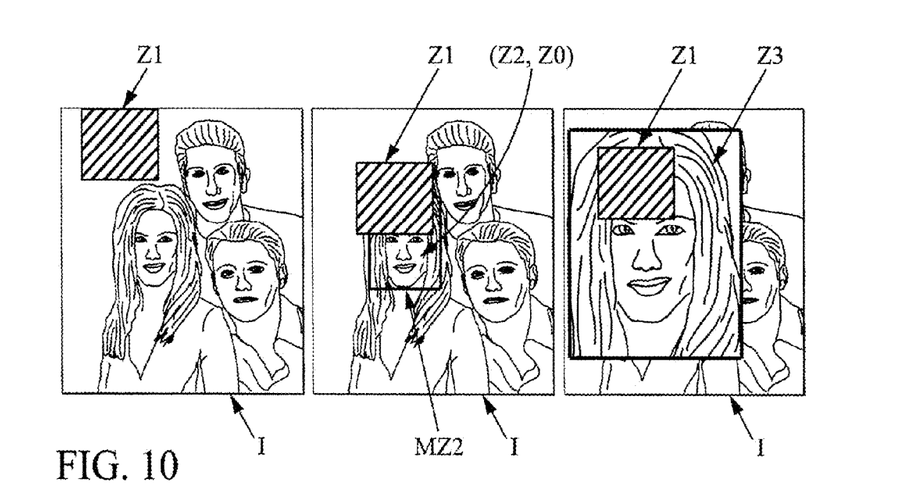
FIG. 10 illustrates the first embodiment of the method according to the invention.

The method according to its first embodiment illustrated in FIG. 10 is essentially such that the shape recognition software comprises an algorithm for segmenting objects with respect to the background which is based on the principle of the figure-background segregation employed in automatic image processing.

The method according to this first embodiment is thus advantageously tailored to the local or semi-local recognition of objects, of faces or of geometric shapes.

FIG. 10 shows drawings representing one and the same photo of three people jointly with the blind zone Z1 representing the scotoma of the individual. At least one face of a person out of the three has been recognized as object to be enhanced. As illustrated in the photo at the center of FIG. 10, the individual bringing, according to the positioning criterion described above, the blind zone onto this face sees a (black) outline appear around the latter so that he/she is informed of the possibility offered to him/her of enhancing the face recognized for example in the manner illustrated in the right-hand drawing of FIG. 10.

According to a particular feature of the first embodiment of the method S, the predetermined processing of the zone of interest Z2 consists as represented in the right-hand photo of FIG. 10 of the magnification of the size of the zone of interest Z2, or equivalently of the object zone ZO, comprising the recognized object. Furthermore, it is proposed according to this embodiment that this magnification be progressive in size until it occupies on the display device D the vision zone Z3. This magnification can moreover be driven directly by the individual for example via the thumbwheel of his/her mouse.

Optionally a progressive shifting of the object zone ZO from its initial position in the digital image I can advantageously be carried out so that the enhanced object is situated at the center of the vision zone, above all when the position of the vision zone Z3 with respect to the blind zone Z1 is chosen as corresponding to the position of the preferred retinal locus PRL zone.

According to this particular feature of its first embodiment, the method S can furthermore comprise a step of return to the digital image I before enhancement consisting of an inverse progressive decreasing of the size of the enhanced zone of interest Z2, and optionally of an inverse progressive shifting of its position, until its return to its size and its position before enhancement.

The method according to this particular feature of the first embodiment thus advantageously allows the individual to preserve a memory of the initial position of the zone of interest in the digital image, especially so as to facilitate subsequent visual exploration of the remainder of the digital image. Shifting the position of the enhanced zone of interest Z2 furthermore makes it possible to advantageously make the vision zone Z3 coincide best with the preferred retinal locus PRL zone determined for each individual.

According to its second embodiment, the method S relates more particularly to a method for assisting reading on a display device of a text intended to be read by an individual afflicted with a retinal pathology manifested by a scotoma is described hereinbelow with reference to FIGS. 1 to 9.

The text forms part of a digital image I composed of a matrix of points. Like any matrix of points, the one making up the image of the text is segmentable into zones. Each zone preferentially consists of a single piece.

In order for the method according to the invention to make it possible to best assist the reader, it may firstly be proposed to preserve, on the display device D, the maximum of global information on the text, especially so that the individual can get his/her bearings easily without being compelled to displace the image permanently, for example with the aid of scrollbars.

To this end, the method comprises a step consisting in modifying the image of the text. This modification can consist of a redimensioning of the digital image I. For example, the image of the text is redimensioned so that the lines of the text begin at an edge of the display device D on which the image of the text is displayed and terminate before an opposite edge of the display device, so that it is not necessary for the reader to displace the image, in the course of the reading thereof, with a corresponding scrollbar at the end and at the start of each line of the text.

Such a redimensioning may automatically induce a modification of the line spacing, but it is also suggested that the latter modification may be effected independently.

This step of modifying the image is preferentially carried out by taking into account at least one parameter out of: the size of the characters, the length and/or the number of lines, the size of the display device and/or the size of a so-called blind zone Z1 representing the scotoma of the individual on the display device. For example, the image of the text is redimensioned so that the blind zone does not overlap more than two successive line portions.

Figure 8:
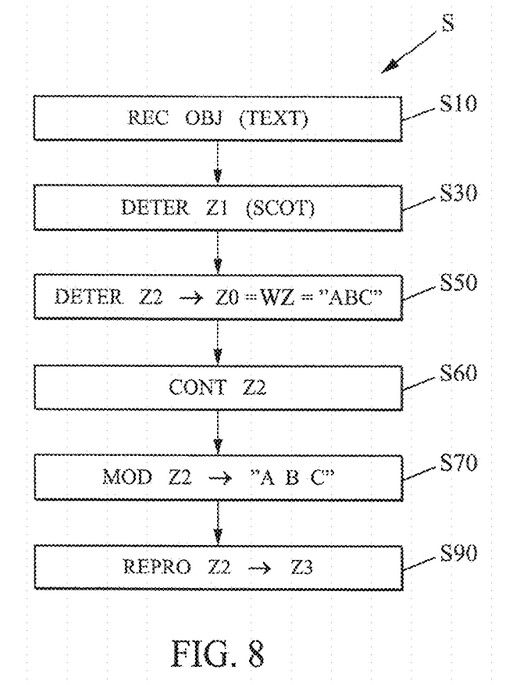
FIG. 8 represents a flowchart of the steps of the method according to its first and second embodiments.

With reference to FIG. 8, the method according to the invention comprises a step consisting in recognizing S10, with the aid of character recognition software, at least one text part by its segmentation into line zones LZ, and then by the segmentation of each line zone into word zones WZ. The recognition software designates a computer method for translating images of printed or typewritten texts into text files, such as optical character recognition (OCR) software. When the word zone segmentation of the image is performed, the coordinates of each word are detected so as to be able to be used.

With reference to FIG. 8, the method according to the invention furthermore comprises a step consisting in determining S30 the blind zone Z1. This blind zone represents the scotoma of the individual on the display device D. Preferably, this blind zone contains the scotoma completely. The shape of this zone may for example be tailored to the shape of the scotoma of an individual, generally approximately of the shape of a disk, or be defined by default, for example as a rectangular shape.

The method according to its second embodiment furthermore comprises a step consisting in determining S50 a zone of interest Z2 comprising at least one word zone WZ.

According to the second embodiment of the method, the positioning and overlap criteria are such as described hereinabove. Thus, as a function of the strategy adopted by the individual, the words included in the zone of interest Z2 may for example be situated under or in proximity to the edges of the blind zone Z1.

According to the second embodiment of the method, the few simple geometric calculations necessary for the determination of a larger area of overlap are based on the detection of the coordinates of each word zone and optionally of each letter zone. It should be noted that, as illustrated by a comparative analysis of FIGS. 4c and 4d, the successive line zones and word zones are not necessarily juxtaposed, for example in such a way that the sum of all the zones covers the image of the text completely, but may on the contrary be spaced slightly apart by empty text zones.

Just as according to the first embodiment of the method, the zone of interest Z2 determined according to one of the positioning or overlap criteria previously described is displayed S60 on the display device via a marking MZ2 allowing the viewing thereof.

With reference to FIG. 8, the method according to the invention furthermore comprises a step consisting in modifying S70 the zone of interest Z2 according to at least one predetermined processing and a step consisting in reproducing S90 the zone of interest Z2 processed in a vision zone Z3 situated at the periphery of the blind zone Z1. Modification S70 and reproduction S90, or reproduction S90 alone, are for example controlled by the individual by pressing a button of the mouse or a key of the keyboard.

According to the second embodiment of the method, the recognition S10 of said at least one text part furthermore comprises the segmentation of each word zone into letter zones. The method thus advantageously allows more finely controlled modification S70 and reproduction S90 of the words situated in the zone of interest, for example by a deformation by winding of the letters of the group of words to be enhanced or by an increasing of the size of the letters furthest from the center of the scotoma which is more considerable than that of the letters closest to the center of the scotoma. When the segmentation of the image into letter zones is performed, the coordinates of each letter zone are detected so as to be able to be used.

The enhancement performed according to the second embodiment of the method advantageously takes account of fundamental aspects taken on by exercise of reading in the presence of a macular scotoma. Indeed, this enhancement does not make do with displacing the information masked by the scotoma (by redimensioning or deformation of the image of the text), but recognizes the words of the image, makes it possible to specifically identify those that the individual wishes to read and optimizes the display of these words so as to compensate the factors that limit reading in the presence of a scotoma. However, these advantages while remaining inaccessible, without segmentation of the image into words, cannot be achieved via this characteristic alone which must be combined with steps S50, S70 and S90 of the method according to the second embodiment of the method in order to assist the reader intelligently and effectively.

To appreciate this better, it is necessary to explain certain notions of visual neurosciences such as preferred retinal locus zone (PRL), visual crowding, acuity and visual span. These notions make it possible to act both from the perceptive standpoint and from the oculomotor standpoint.

Figure 1:
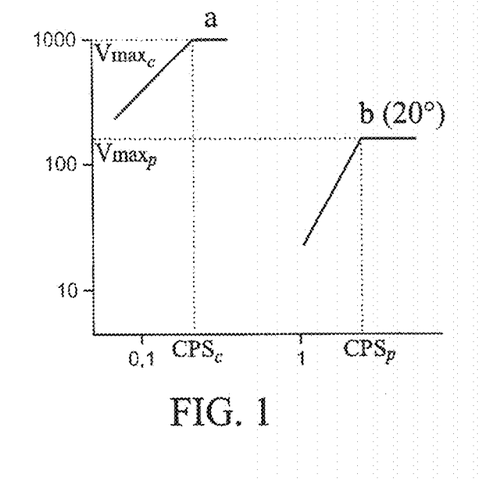
FIG. 1 illustrates the evolution of maximum reading speeds under central vision and under peripheral vision as a function of the size of the characters read.

With reference to FIG. 1, it has been established that acuity under eccentric vision benefits from a gain in terms of reading speed when the size of the characters of the text is increased. However, simply increasing the size of the characters in peripheral vision (b), in healthy individuals under conditions of high-speed presentation of successive visual objects or RSVP (for Rapid Serial Visual Presentation), does not make it possible to achieve the speed thresholds obtained in foveal vision (a). The graph of FIG. 1 (Legge et al. 1985a; Legge et al. 1985b) shows reading speed measurements, plotted as ordinate, as a function of the size of the characters read, plotted as abscissa. FIG. 1 therefore illustrates reading performance as a function of size of characters for individuals using their normal vision (a) and individuals using their peripheral vision (b).

Figure 2:
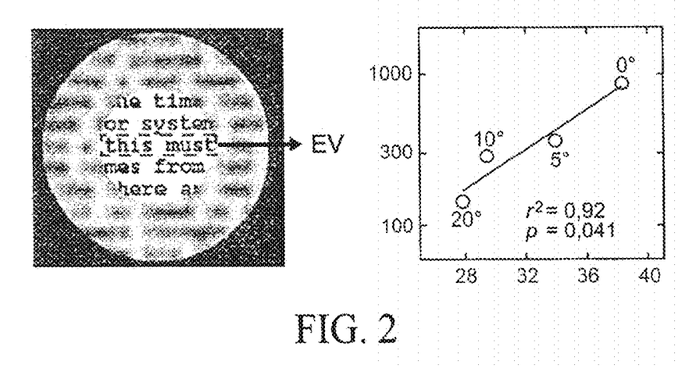
FIG. 2 illustrates the visual span (on the left) and the effect of the size of the visual span on reading speed (on the right), each of FIGS. 3a and 3b illustrates the phenomenon of visual crowding and a mode of suppressing this phenomenon according to the invention.

With reference to FIG. 2, the visual span is defined as an essential notion within the framework of studies on reading. It corresponds to the extent of the visual field in which the letters can be identified outside of any linguistic information. It quantifies the number of letters which can be identified on the basis of a fixation without resorting to context. The image on the left of FIG. 2 illustrates the notion of visual span (VS). If the individual's gaze fixes on the center of the circle containing the words, their visual span then corresponds to the words "this must". The graph on the right of FIG. 2 (O'Regan 1979 and O'Regan et al. 1983) presents the effect of the size of the visual span (as abscissa) on reading speed (as ordinate). This image shows the following phenomenon: reading speed increases with the size of the visual span.

Figure 3A:
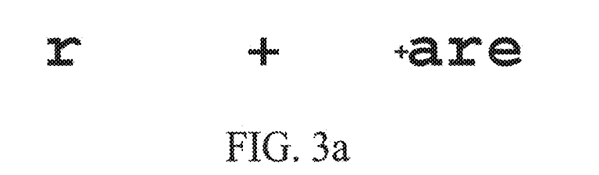

With reference to FIG. 3a, visual crowding is the product of a spatial interaction between adjacent letters of a word, or between the words themselves. If the letter (or the word) to be identified possesses a sufficiently large spatial zone of isolation, the crowding does not act on its identification. Conversely, when other letters (or words) are present inside this zone, identification of the letter in question is disturbed. The size of the spatial zone (called the isolation zone) necessary to avoid the phenomenon of visual crowding increases in proportion to eccentricity. FIG. 3a makes it possible to demonstrate this. When fixing on the middle cross, it is easy to identify the letter "r" on the left. However, the letter "r" on the right is impossible to identify; to identify it, it is necessary to fix on the small cross situated on the left of the letter "a" (Pelli and Tillman, 2007).

The preferred retinal locus PRL zone is defined as the vision zone toward which attention is deployed, in the presence of a scotoma. Indeed, when a central scotoma is present, the center of the retina cannot be used to identify a target and the individual is compelled to deploy his/her attention outside the afflicted region by thus dissociating his/her gaze from the zone of deployment of attention. The preferred retinal locus zone is therefore spontaneously displaced, in the presence of a scotoma, toward one or more vision zones Z3 of the extrafoveal retina. During a task of fixation of a target by an individual, these preferred retinal locus zones are detectable and positionable, for example with the aid of an oculometer.

Thus, it is clearly apparent that, prior to the determination S50 of the zone of interest Z2, the step consisting in modifying the image of the text makes it possible to set the characters of the text to a size which allows the individual to read each of the words by placing him/herself at the word acuity threshold as a function of the size of the scotoma. This size of the characters of the text is sufficiently large to allow the individual to have a correct reading with his/her scotoma, but not too large to avoid loss of global information on the text. The line spacing of the text can be increased, as a function of the size of the scotoma, so that the individual can better position his/her scotoma on the line while reading.

Figure 3B:
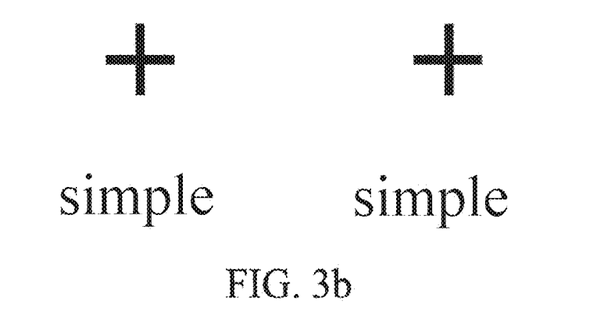

With reference to FIG. 3b, according to a particular feature of the second embodiment of the method, said at least one predetermined processing of the zone of interest Z2 consists of a segmentation of each word zone into character zones (or letter zones) and in an increasing of the spacing between the characters, so as to make it possible to limit, or indeed to avoid, the phenomenon of visual crowding. FIG. 3b illustrates this by showing, on the left, a word whose spacing between letters is normal, thereby rendering its identification in eccentric vision difficult (when fixing on the cross on the left), and on the right, a word whose spacing between letters is increased, thereby rendering its identification in eccentric vision easier (when fixing on the cross on the right).

According to another particular feature of the second embodiment of the method, the zone of interest Z2 can comprise, in addition to said at least one overlapped word zone, at least two other word zones belonging to the same line zone, each word zone of the zone of interest Z2 being preferentially juxtaposed with another word zone of the zone of interest Z2. The method thus advantageously makes it possible to take into account the size of each word zone and to tailor the assistance afforded the individual to his/her visual span.

Furthermore, according to another particular feature of the second embodiment of the method, which particular feature was already introduced hereinabove with reference to the first embodiment of the method, at least one zone out of the blind zone Z1 and the vision zone Z3 comprises a visible marking on the display device. The method according to this particular feature thus advantageously makes it possible to further aid the individual to stabilize vertically on the line that he/she is in the process of reading. Furthermore, as illustrated in FIGS. 4a to 4d, the blind zone Z1 is delimited by an outline and the presence of this outline aids the individual to be aware of the boundaries of his/her blind spot and allows him/her to optimize his/her ocular movements.

Figure 4A:
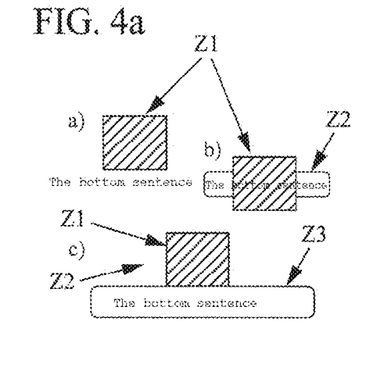
FIGS. 4a, 4b, 4c and 4d illustrate several variants of the second embodiment of the method according to the invention.

In the example illustrated in FIG. 4a, from a high position with respect to a sentence of the text, the blind zone Z1 is brought by the individual by virtue of the pointing device onto the group of words that they wish to enhance. The zone of interest Z2 is displayed to aid the individual to position him/herself on his/her target. The predetermined processing or enhancement of the zone of interest Z2 consists according to this example in an increase of its size, the amplitude of the increase possibly for example depending on the size of the blind zone Z1.

Figure 4B:
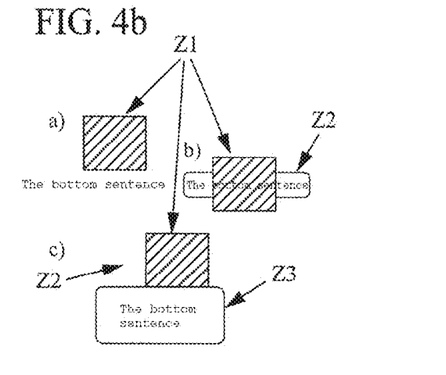
Figure 4C:
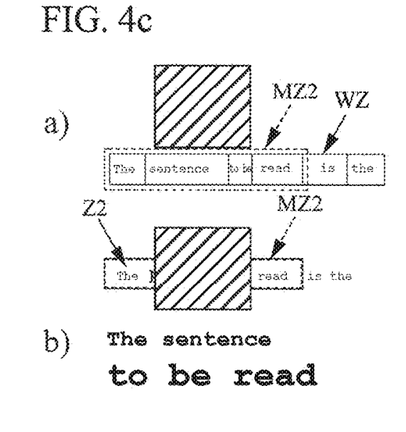
Figure 4D:
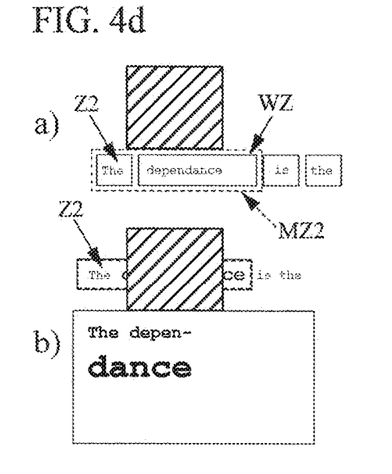

It should be noted that, in FIG. 4a, as in FIG. 4b, the blind zone Z1 is made transparent so as to see the words that it overlaps, whereas, in a real situation, the words overlapped by the blind zone are hidden from the individual by his/her scotoma and are therefore invisible, as is illustrated in FIGS. 4c and 4d.

In the example illustrated in FIG. 4b, the method S according to its second embodiment is implemented in a manner identical to the example discussed hereinabove with reference to FIG. 4a, except that the enhancement of the zone of interest Z2 consists not only of an increasing of its size, but also in a distributing of the words that it comprises over several lines, in this instance two lines, of the vision zone Z3.

In the example illustrated in FIG. 4c, the method S is implemented in a manner identical to the example discussed hereinabove with reference to FIG. 4b, except that the enhancement of the zone of interest Z2 furthermore consists in that the size of the characters and/or the spacing between the characters are further increased as the characters are reproduced S90 on a line of the vision zone Z3 further from the blind zone Z1.

In the example illustrated in FIG. 4d, the method S is implemented in a manner identical to the example discussed hereinabove with reference to FIG. 4c, except that the zone of interest Z2 comprises a long-word zone WZ and the enhancement of this zone of interest furthermore consists of a breaking of the long word.

Figure 5:
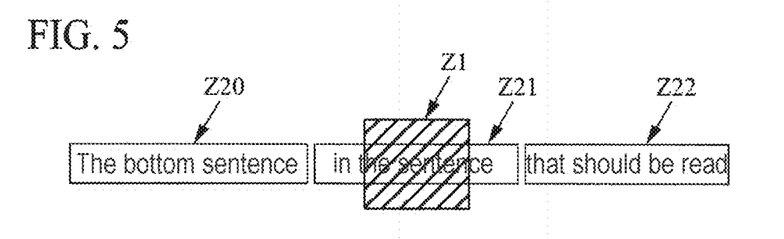
FIG. 5 illustrates a particular feature of the second embodiment of the method according to the invention.

According to one embodiment of the method, and as illustrated in FIG. 5, a previous zone of interest Z20 and/or a following zone of interest Z22 situated respectively on either side of a current zone of interest Z21 (determined in step S50) are furthermore determined. In the example illustrated in FIG. 5, each zone Z20, Z21 and Z22 comprises an outline which is visible on the display device.

Figure 6:
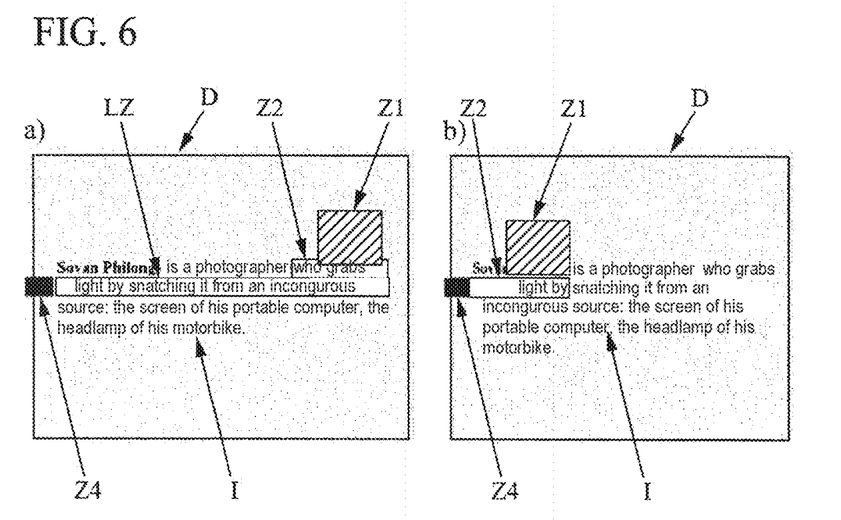
FIG. 6 illustrates another particular feature of the second embodiment of the method according to the invention.

According to a particular feature of its second embodiment, and with reference to FIG. 6, the method furthermore comprises a step consisting in displaying on the display device a frame Z4 on the left of the line zone situated directly below the line zone comprising the zone of interest Z2. Line transfer is a considerable problem when reading a text in eccentric vision. FIG. 6 shows how a frame Z4, here a black rectangle, on the left of the text can aid in locating the start of a following line zone LZ. In this example, the method S makes it possible to choose the words situated under the lower edge of the scotoma. The black rectangle is displayed when the individual places the edge of his/her scotoma on a zone of interest Z2 of a line zone LZ which is situated just above and remains for example displayed for a few seconds, for example for 3 seconds. Thus, when the individual transfers from one line to another (right image), the zone of interest Z2 is just alongside the black rectangle Z4. If the individual misses the line, the black rectangle Z4 is not on the same line as the zone of interest Z2 and the individual thus perceives that he/she is not situated on the subsequent line.

According to a particular feature of the first and second embodiments of the method S, a test aimed at choosing the preferred retinal locus PRL zone, optionally vertical, of the individual is performed so as to display the enhanced words in an optimal position of the individual's visual field.

Thus, according to this embodiment, the method S comprises, prior to the reproduction S90 in the vision zone Z3 of the processed zone of interest Z2, a step consisting in determining the peripheral position of the vision zone Z3 with respect to the blind zone Z1 as corresponding to the position of a preferred retinal locus zone determined for each individual, for example by taking into account the position and the size of his/her scotoma.

Figure 7A:
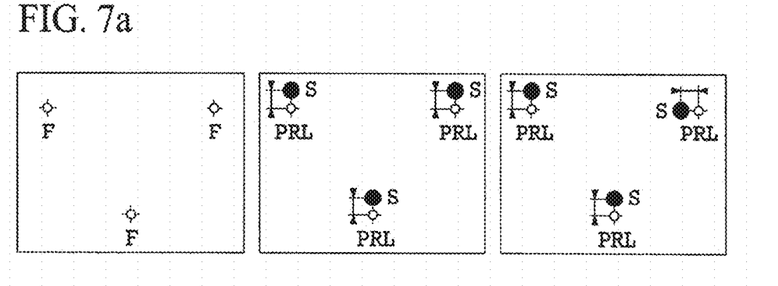
FIGS. 7a and 7b illustrate an embodiment of the determination of the peripheral position of the vision zone with respect to the blind zone.

More particularly according to this embodiment, and with reference to the two images on the left of FIG. 7a, the determination of the peripheral position of the vision zone Z3 with respect to the blind zone Z1 comprises the calibration steps consisting in:
  displaying on the display device a plurality of targets F,
  for each target F, detecting, with an oculometer, the relative position of the scotoma S of the individual with respect to the target when the individual fixes on the target, and
  calibrating the position of the preferred retinal locus PRL zone as being the relative position of the target F with respect to the position of the scotoma S.

This calibration is sufficient if, for each target F, the relative position of the scotoma S with respect to the target is the same. In the converse case, a correction of the calibration has preferentially to be considered which may be according to the following variant.

Figure 7B:
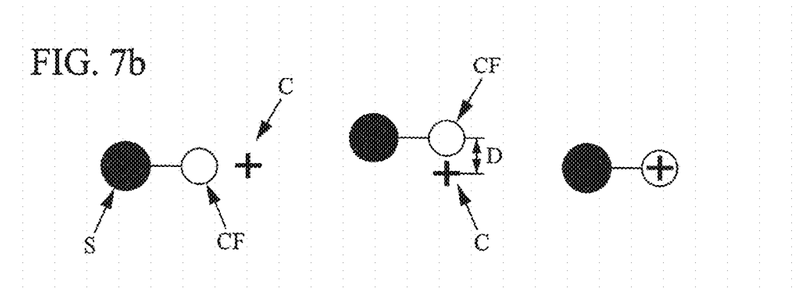

According to this variant, and with reference to the image on the right of FIG. 7a and to FIG. 7b, if the relative position of the scotoma S with respect to the position of the target F varies as a function of the target, the determination of the peripheral position of the vision zone Z3 with respect to the blind zone Z1 comprises the calibration steps consisting in:
  displaying on the display device a plurality of targets F,
  for each target F, detecting, with an oculometer, the relative position of the scotoma S of the individual with respect to the target when the individual fixes on the target,
  calibrating the position of the preferred retinal locus PRL zone as being the relative position of the target with respect to the position of the scotoma, slaving, as a function of the calibration carried out according to the previous detections, the positioning of a shape outline SO displayed on the display device to the positioning of the scotoma S detected by the oculometer, displaying a fixed target symbol T on the display device, measuring the shift d between the slaved shape outline and the target symbol, when the individual to be positioned the slaved shape outline SO so as to include therein the target symbol T, and correcting, as a function of this measurement, the calibration carried out according to the previous detections, so as to calibrate the relative position of the preferred retinal locus zone with respect to the position of the scotoma.

According to another variant of the test aimed at choosing the preferred retinal locus zone of the individual, the individual him/herself can manually adjust the vision zone Z3 to optimize his/her comfort of use.

The vision zone Z3 or RAV (for Region of Augmented Vision) is then preferentially displayed on the preferred retinal locus PRL zone of the individual.

In all the examples set forth hereinabove relating to the second embodiment of the method, the individual's preferred retinal locus PRL zone is assumed to have been determined according to the test described hereinabove as being vertical and situated under the scotoma, so that, as represented, the vision zone Z3 is situated vertically in line with the blind zone Z1 and under the latter.

According to a particular feature of the second embodiment of the method, the center of the vision zone Z3 is preferentially aligned with the center of the blind zone Z1, thereby allowing the individual to identify the largest number of letters in a single fixation and to thus increase his/her visual span.

It should be noted that, according to the second embodiment of the method, the zone of interest Z2 remains preferentially visible while the vision zone Z3 is displayed.

According to the second embodiment of the method, that the zone of interest Z2 is situated in proximity to an edge of the display device D so that the vision zone Z3 would be only partially reproduced on the display device D according to said predetermined processing may also induce a limitation of the zone of interest to the word zone being as close as possible to the edge of the display device. In which case, the method advantageously provides that other word zones situated, in the same line zone, on a side opposite to the edge of the display device is also selected as lying in the zone of interest so as to continue to profit fully from the visual span of the individual, including in this situation.

It should also be noted that, according to the second embodiment of the method, segmenting the text of the image into word zones makes it possible to reproduce S90 complete words in the vision zone Z3.

It should further be noted that, according to the second embodiment of the method, the text of the image may be completely recognized S10 in one go by the character recognition software. However, in a nonlimiting manner, just a part of the text may be recognized which would for example be selected by the reader on the image by a mouse movement together with pressing of the left button thereof. Another part of the text could thereafter be selected in the same manner. By another example, only a part of the text line overlapped by the blind zone or a text part situated around the blind zone is recognized S10. Furthermore, the recognition S10 and the other steps S30 to S90 of the method may be triggered by the individual by pressing a button of the mouse or a key of the keyboard.

The method according to the invention is implemented on a computer comprising at least one processor suitable for executing a computer program comprising instructions for the implementation of the method.

It should be obvious to persons versed in the art that any reference to a text line is to be considered with regard to the writing and reading of a given language.

Hence, depending on the language considered, it will be possible to consider a column instead of a line, without straying from the invention as claimed. Likewise, the previous Z20, current Z21 and following Z22 zones of interest such as illustrated in FIG. 5 illustrate a direction of reading from left to right, while certain other languages, such as Arabic, use an opposite direction of writing and reading.

The present invention also envisages a computer program comprising instructions for the implementation of the method hereinabove, when this program is executed by a processor. It also envisages a medium (non-transient especially) storing such a program. The computer program may be written in various programming languages, such as for example the Python™ language. Furthermore, this program may be based on programming applications and/or interfaces intended to facilitate the development thereof; an application of this type is for example known by the commercial term PsychoPy™ and a programming interface of this type is for example the OpenGL™ interface.

As described above, the method according to the invention can be implemented by using various items of hardware to facilitate the visual exploration of various digital contents.

As a first example given by way of nonlimiting illustration, the display device can consist of a computer screen or tablet screen and the content considered can consist of a digital book or a virtual visit. The content can then be processed according to the method in a manner simultaneous with its visual exploration or upstream of a or of any visual exploration. More particularly, the digital content of the virtual visit, of an art gallery for example, can be preprocessed by recognizing therein the works of art which are exhibited therein as objects included in object zones, so that said zones can be enhanced according to the method of the invention during all forthcoming visual explorations so as to facilitate for any user the visual exploration of the works of art exhibited.

As a second example given by way of nonlimiting illustration, the display device may consist of lenses of video or multimedia spectacles possibly connected to a communication network, such as the Internet, and the digital image I displayed on the spectacle lenses can then consist of all or part of a picture of the spectacle wearer's visual field. This picture can be captured by a camera arranged on the spectacles and refreshed continuously so as to be representative of what, at each instant, the wearer sees through his/her spectacles. The recognition of objects in this picture can then also be carried out continuously, for example the faces of the people situated in the wearer's visual field may be recognized as objects included in object zones, so that said zones may be enhanced according to the method of the invention, at least so as to facilitate for the wearer the identification of said people. In this sense, the enhanced object zone may also be refreshed continuously so as to be representative of the movements, and more generally of any evolution over time, of the recognized objects. First results have been obtained for the recognition of objects and more particularly, of faces of people situated in the visual field of a wearer.

Some twenty or so wearers afflicted with ARMD were subjected to the following test of identification of faces. Nine faces are displayed on an image presented to the wearers: one face at the center and eight faces around. The task consists in finding, among the faces which are around, the face which corresponds to the middle one and in reading the digit which is inscribed on the selected face. The 8 faces present in the image are the same throughout the test, only the orientation changes and the expression on their face and the face situated in the center varies from test to test. This face recognition was performed without visual aid and with the method for assisting visual exploration according to the invention.

A parametric test (Student's test) demonstrated a significant difference of the order of 31% between recognition without visual aid and recognition with the method for assisting visual exploration according to the invention, in favor of the latter. This result is very encouraging since it shows a considerable increase in the performance of wearers afflicted with ARMD during recognition of faces of people in their visual field, when these wearers use the method for assisting visual exploration according to the invention.

The invention claimed is:

1. A method (S) for assisting visual exploration of a digital image (I) on a display device by a user afflicted with a retinal pathology manifested by a scotoma, the digital image being composed of a matrix of points which is segmentable into zones, the method comprising the steps of:
recognizing (S10), using shape recognition software, at least one object contained in an object zone (ZO) of the digital image;
determining (S30) a blind zone (Z1) in the image, corresponding to a position of the scotoma in the field of vision of the user looking at the image;
in case of detection of a proximity of the blind zone and of the object zone, applying a processing of the image, for highlighting (S70, S90) the object zone for the user;
determining (S50) a zone of interest (Z2) comprising at least one object zone (ZO), according to a criterion of positioning of the blind zone (Z1) on the digital image, the blind zone being positionable on the display device by slaving to a pointing device; and
displaying (S60) on the display device a marking (MZ2) allowing the viewing of the determined zone of interest (Z2),
wherein the highlighting (S70, S90) of the object zone comprises enhancing the determined zone of interest (Z2) by modifying the determined zone of interest (S70) and by reproducing the determined zone of interest (S90) in a vision zone (Z3) according to at least one predetermined processing.

2. The method as claimed in claim 1, wherein the criterion, according to which the zone of interest (Z2) is determined, of positioning of the blind zone (Z1) on the digital image (I) is chosen from among:
a criterion of overlap of the zone of interest (Z2) by the blind zone (Z1), and
a criterion of overlap of the zone of interest (Z2) by a preferred retinal locus zone (PRL) determined for each individual, the positioning of this preferred retinal locus zone (PRL) on the display device (D) relating to the positioning of the blind zone (Z1) on this same device.

3. The method as claimed in claim 2, wherein said criterion of overlap comprises determining:

the positioning of a specific point of the blind zone (Z1) or of the preferred retinal locus zone (PRL) on the zone of interest (Z2), or
a larger area of overlap of the zone of interest (Z2) by the blind zone (Z1) or by the preferred retinal locus zone (PRL).

4. The method as claimed in claim 1, wherein, when the zone of interest (Z2) is situated in proximity to an edge of the display device (D) so that the vision zone (Z3) would be only partially reproduced on the display device (D) according to said predetermined processing, the enhancement of the zone of interest (Z2) further comprises displacing the vision zone (Z3) in such a way that the vision zone (Z3) is completely reproduced on the display device (D) and exhibits a substantially maximum overlap with the vision zone (Z3) which would be only partially reproduced on the display device (D) according to said predetermined processing.

5. The method as claimed in claim 1, wherein the highlighting (S70, S90) of the object zone is controlled by an individual by actuating, and optionally by keeping actuated, an actuator, and the method further comprises a step of return to the digital image (I) before enhancement, this return being controlled by the individual by actuation, and optionally by release, of the actuator, respectively.

6. The method as claimed in claim 1, wherein at least one zone out of the blind zone (Z1) and the vision zone (Z3) comprises a visible marking on the display device.

7. The method as claimed in claim 1, wherein the shape recognition software comprises an algorithm for segmenting objects with respect to the background which is based on the principle of the figure-background segregation employed in automatic image processing.

8. The method as claimed in claim 1, wherein the predetermined processing of the zone of interest (Z2) comprises the progressive magnification of the zone of interest's size and optionally the zone of interest's progressive shifting from an initial position in the digital image (I) until the zone of interest occupies on the display device (D) the vision zone (Z3) and the method further comprises a step of return to the digital image (I) before enhancement consisting of a progressive decreasing of the size of the enhanced zone of interest (Z2) and optionally a progressive shifting of the zone of interest's position until the zone of interest returns to the zone of interest's size and the zone of interest's position before enhancement.

9. The method as claimed in claim 1, wherein the method (S) for assisting visual exploration is a method for assisting reading; the digital image (I) comprises a text intended to be read; the shape recognition software comprises character recognition software, making possible to recognize at least one text part by segmentation of the text into line zones (LZ), and then by the segmentation of each line zone (LZ) into word zones (WZ); the object zone (ZO) is a word zone (WZ); and the vision zone (Z3) is situated at the periphery of the blind zone (Z1).

10. The method as claimed in claim 9, further comprising, prior to the determination (S50) of the zone of interest (Z2), a step of modifying the image of the text by re-dimensioning the text and/or by modification of the line spacing as a function of the size of the characters, of the length and/or of the number of the lines, of the size of the display device and/or of the size of the blind zone.

11. The method as claimed in claim 9, wherein the recognition (S10) of said at least one text part further comprises the segmentation of each word zone (WZ) into letter zones.

12. The method as claimed in claim 9, wherein the zone of interest (Z2) comprises, in addition to said at least one word zone (WZ), at least two other word zones belonging to the same line zone (LZ), each word zone of the zone of interest (Z2) being juxtaposed with another word zone of the zone of interest (Z2).

13. The method as claimed in claim 9, wherein said at least one predetermined processing of the zone of interest (Z2) comprises:
- a segmentation of each word zone (WZ) into character zones, and/or
- an increasing of the size of the characters optionally as a function of the size of the blind zone (Z1), and/or
- a change of character font, and/or
- a layout of the words over several lines, and/or
- a breaking of a word, and/or
- an increasing of the spacing between the characters, and/or
- a modification of the contrast, and/or
- a polarity inversion, and/or
- a voice synthesis of the words contained in the zone of interest (Z2).

14. The method as claimed in claim 13, wherein the size of the characters and/or the spacing between the characters are further increased as the characters are intended to be reproduced (S90) on a line of the vision zone (Z3) further from the blind zone (Z1).

15. The method as claimed in claim 9, wherein a previous zone of interest (Z20) and/or a following zone of interest (Z22) are furthermore determined (S50), situated respectively on either side of a current zone of interest (Z21), at least one of these zones comprising a visible marking on the display device.

16. The method as claimed in claim 9, further comprising a step of displaying on the display device (D) a frame (Z4) on the left of the line zone (LZ) situated directly below the line zone comprising the zone of interest (Z2).

17. The method as claimed in claim 9, wherein the vision zone (Z3) is situated in a juxtaposed and centered manner below or above the blind zone.

18. The method as claimed in claim 1, further comprising, prior to the reproduction (S90) in the vision zone (Z3) of the processed zone of interest (Z2) or prior to the determination (S50) of the zone of interest (Z2) according to a choice of positioning criterion, a step of determining the peripheral position of the vision zone (Z3) with respect to the blind zone (Z1) as corresponding to the position of a preferred retinal locus zone (PRL) determined for each individual.

19. The method as claimed in claim 18, wherein the determination of the peripheral position of the vision zone (Z3) with respect to the blind zone (Z1) comprises the calibration steps of:
- displaying on the display device a plurality of targets (F),
- for each target, detecting, with an oculometer, the relative position of the scotoma (S) of the individual with respect to the target (F) when the individual fixes on the target, and
- calibrating the position of the preferred retinal locus zone (PRL) as being the relative position of the target (F) with respect to the position of the scotoma, and
- if, the relative position of the scotoma (S) with respect to the position of the target (F) varies as a function of the fixed target (F),
- slaving, as a function of the calibration carried out according to the previous detections, the positioning of a shape outline (SO) displayed on the display device to the positioning of the scotoma detected by the oculometer,
- displaying a fixed target symbol (T) on the display device,
- measuring the shift (d) between the slaved shape outline (SO) and the target symbol, when the individual to be positioned the slaved shape outline so as to include therein the target symbol (T), and
- correcting, as a function of this measurement, the calibration carried out according to the previous detections.

20. The method as claimed in claim 1, wherein the pointing device slaving the positioning of the blind zone (Z1) is chosen from among a computer keyboard, a mouse and an oculometer.

21. A non-transitory computer-readable storage medium with an executable program stored thereon, wherein the program instructs a microprocessor to perform the steps of the method according to claim 1.

22. The method as claimed in claim 1,
wherein the predetermined processing of the zone of interest (Z2) comprises the progressive magnification of the zone of interest's size and progressive shifting the zone of interest from an initial position in the digital image (I) until the zone of interest occupies on the display device (D) the vision zone (Z3), and
the method further comprises a step of return to the digital image (I) before enhancement that includes a progressive decreasing of the size of the enhanced zone of interest (Z2) and a progressive shifting of the enhanced zone of interest's position until returning to the enhanced zone of interest's size and the enhanced zone of interest's position before enhancement.

* * * * *